United States Patent
Hwang et al.

(10) Patent No.: US 9,924,898 B2
(45) Date of Patent: Mar. 27, 2018

(54) FLASH ACTIVATED PASSIVE SHIELDING NEEDLE ASSEMBLY

(75) Inventors: Charles G. Hwang, Ridgewood, NJ (US); Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 770 days.

(21) Appl. No.: 12/103,322

(22) Filed: Apr. 15, 2008

(65) Prior Publication Data
US 2009/0259201 A1 Oct. 15, 2009

(51) Int. Cl.
*A61B 5/15* (2006.01)
*A61B 5/145* (2006.01)
(Continued)

(52) U.S. Cl.
CPC .......... *A61B 5/150648* (2013.01); *A61B 5/14* (2013.01); *A61B 5/1405* (2013.01);
(Continued)

(58) Field of Classification Search
CPC .. A61M 5/3213; A61M 5/3243; A61M 5/326; A61M 5/3269; A61M 25/0612; A61M 25/0618; A61M 25/0625; A61M 25/0631; A61M 2205/0216; A61M 5/3205; A61M 5/321; A61M 5/3245; A61M 2005/3247; A61M 2005/3252; A61M 2005/3267; A61M 5/3293; A61M 5/50; A61M 2025/0042; A61M 25/0084; A61M 2025/0089; A61M 2025/0091; A61M 25/0097; A61M 25/0637; A61M 2202/0413; A61M 2205/273; A61M 2210/04; A61M 2210/12; A61B 5/14; A61B 5/1405; A61B 5/1411; A61B 5/15;
(Continued)

(56) References Cited

U.S. PATENT DOCUMENTS 4,964,854 A 10/1990 Luther
4,966,593 A 10/1990 Lennox
(Continued)

FOREIGN PATENT DOCUMENTS

WO 2007122959 A1 11/2007

*Primary Examiner* — Shefali Patel
(74) *Attorney, Agent, or Firm* — The Webb Law Firm

(57) ABSTRACT

A safety needle device includes a housing including a passageway with a needle cannula extending therefrom. A shielding member is movable between a first position in which a puncture tip of the needle cannula is exposed therefrom and a second position in which the puncture tip of the needle cannula is encompassed therein. The shielding member is maintained in the first position against a biasing force which biases the shielding member toward the second position. A fluid and/or a temperature activation material is associated with the shielding member and is adapted to deform upon contact with a fluid medium and/or a certain temperature or temperature range. The fluid medium flowing through the needle cannula causes the fluid activation material to deform, such as through expansion, thereby releasing the shielding member from the first position and allowing a drive member to bias the shielding member toward the second position.

19 Claims, 7 Drawing Sheets

(51) Int. Cl.
  *A61M 5/32* (2006.01)
  *A61M 25/00* (2006.01)
  *A61M 25/06* (2006.01)
  *A61B 5/153* (2006.01)
(52) U.S. Cl.
  CPC .............. *A61B 5/1411* (2013.01); *A61B 5/15* (2013.01); *A61B 5/153* (2013.01); *A61B 5/15003* (2013.01); *A61B 5/15074* (2013.01); *A61B 5/150374* (2013.01); *A61B 5/150389* (2013.01); *A61B 5/150519* (2013.01); *A61B 5/150534* (2013.01); *A61B 5/150633* (2013.01); *A61M 5/321* (2013.01); *A61M 5/3205* (2013.01); *A61M 5/326* (2013.01); *A61M 5/3243* (2013.01); *A61M 5/3269* (2013.01); *A61M 5/3293* (2013.01); *A61M 25/0084* (2013.01); *A61M 25/0097* (2013.01); *A61M 25/0612* (2013.01); *A61M 25/0618* (2013.01); *A61M 25/0625* (2013.01); *A61M 25/0637* (2013.01); *A61B 5/1535* (2013.01); *A61B 5/150259* (2013.01); *A61B 5/150717* (2013.01); *A61B 5/150786* (2013.01); *A61M 2005/3252* (2013.01); *A61M 2025/0042* (2013.01); *A61M 2025/0089* (2013.01); *A61M 2202/0413* (2013.01); *A61M 2205/273* (2013.01); *A61M 2210/04* (2013.01); *A61M 2210/12* (2013.01)
(58) Field of Classification Search
  CPC ........ A61B 5/150007; A61B 5/150015; A61B 5/15003; A61B 5/150206; A61B 5/150374; A61B 5/150534; A61B 5/150633; A61B 5/150885; A61B 5/153; A61B 5/150389; A61B 5/150503; A61B 5/150519; A61B 5/15074; A61B 5/150648
  USPC ........... 604/168.01, 263, 110, 162, 192, 198, 604/126, 127, 190, 500, 506
  See application file for complete search history.

(56) References Cited

U.S. PATENT DOCUMENTS

| | | | |
|---|---|---|---|
| 4,971,068 A | | 11/1990 | Sahi |
| 5,120,317 A | | 6/1992 | Luther |
| 5,149,322 A | * | 9/1992 | Nash .............................. 604/110 |
| 5,176,655 A | | 1/1993 | McCormick et al. |
| 5,192,275 A | | 3/1993 | Burns |
| 5,290,264 A | | 3/1994 | Utterberg |
| 5,554,131 A | * | 9/1996 | Lacivita .............. A61M 5/3243 604/110 |
| 5,562,636 A | | 10/1996 | Utterberg |
| 5,562,637 A | | 10/1996 | Utterberg |
| 5,702,367 A | | 12/1997 | Cover et al. |
| 5,951,525 A | | 9/1999 | Thorne et al. |
| RE36,398 E | | 11/1999 | Byrne et al. |
| RE36,447 E | | 12/1999 | Byrne et al. |
| 7,014,623 B2 | * | 3/2006 | Prestidge .............. A61M 5/321 604/110 |
| 2002/0099339 A1 | | 7/2002 | Niermann |
| 2003/0220587 A1 | * | 11/2003 | Swenson ........... A61M 25/0637 600/576 |
| 2005/0119627 A1 | | 6/2005 | Crawford |
| 2008/0167623 A1 | * | 7/2008 | Iwase et al. .................. 604/198 |
| 2009/0118639 A1 | * | 5/2009 | Moos .................. A61B 10/025 600/567 |

* cited by examiner

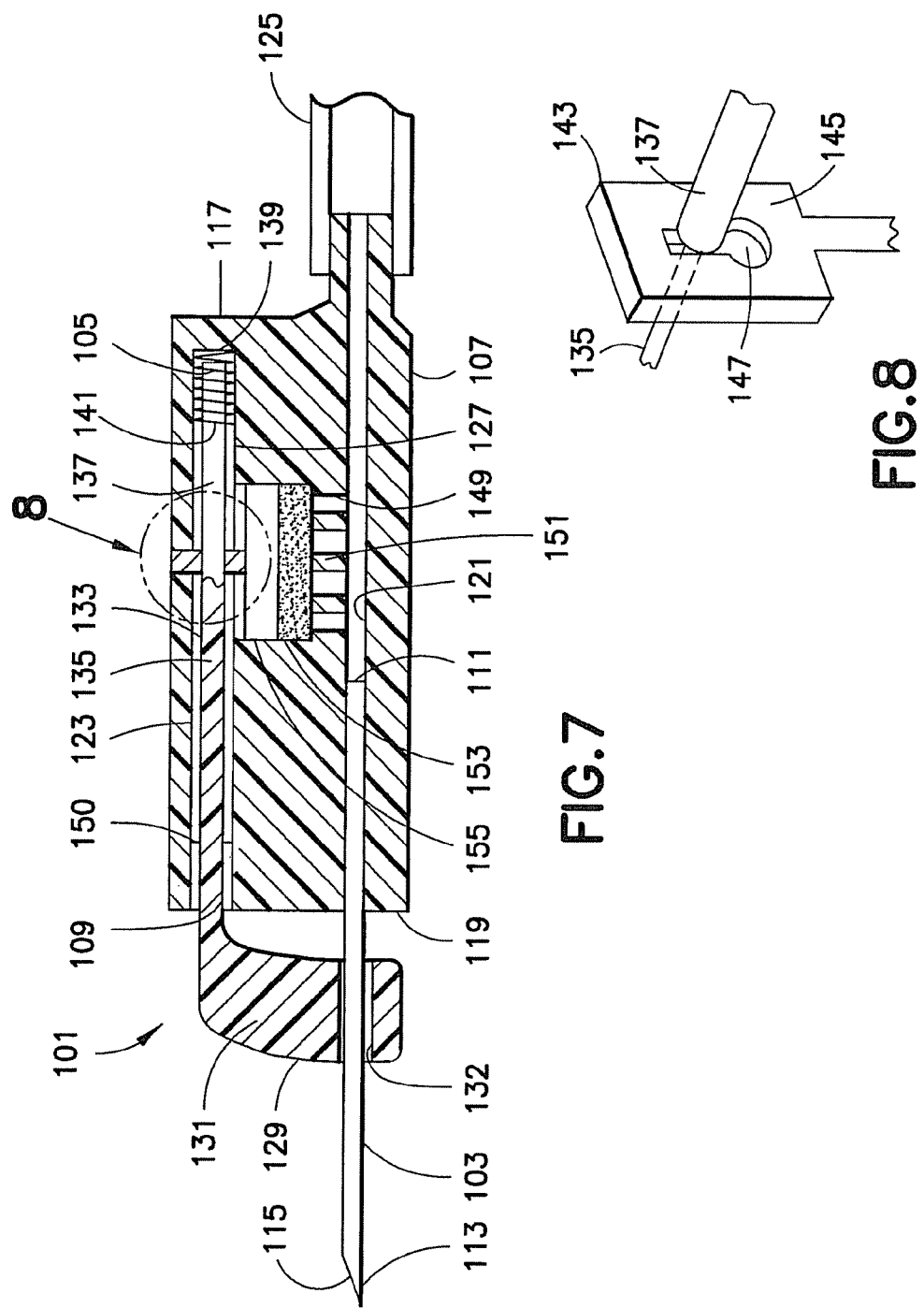

FLASH ACTIVATED PASSIVE SHIELDING NEEDLE ASSEMBLY

BACKGROUND OF THE INVENTION

Field of the Invention

The present invention relates to blood collection sets for safe and convenient handling of needles used in blood collection procedures. More particularly, the present invention relates to a blood collection set including a safety shield for protecting users from a used needle tip.

Description of Related Art

Disposable medical devices having medical needles are used for administering medication or withdrawing fluid from the body of a patient. Such disposable medical devices typically include blood-collecting needles, fluid handling needles, and assemblies thereof. Current medical practice requires that fluid containers and medical needles used in such devices be inexpensive and readily disposable. Existing blood collection devices often employ some form of durable, reusable holder on which detachable and disposable medical needles and fluid collection tubes may be mounted. A blood collection device of this nature may be assembled prior to use and then discarded after use.

A blood collection device or intravenous (IV) infusion device typically includes a needle cannula having a proximal end, a pointed distal end, and a lumen extending therebetween. The proximal end of the needle cannula is securely mounted in a plastic hub defining a central passage that communicates with the lumen extending through the needle cannula. A thin, flexible thermoplastic tube is connected to the hub and communicates with the lumen of the needle cannula. The end of the plastic tube remote from the needle cannula may include a fixture for connecting the needle cannula to a tube holder or other receptacle. The specific construction of the fixture will depend upon the characteristics of the receptacle to which the fixture is to be connected.

In order to reduce the risk of incurring an accidental needle-stick wound, protection of used needle cannulas becomes important. With concern about infection and transmission of diseases, methods and devices to enclose or cover the used needle cannula have become very important and in great demand in the medical field. For example, needle assemblies often employ a safety shield that can be moved into shielding engagement with a used needle cannula to minimize risk of an accidental needle stick.

Some needle safety shields are referred to as "tip guards" and include a small rigid guard that may be telescoped along the length of the needle cannula and extended over the pointed distal end of the needle cannula for protection. Such conventional tip guards may include some form of tether for limiting the travel of the tip guard to the length of the needle cannula. An example of the foregoing is disclosed by U.S. Pat. No. 5,176,655 to McCormick et al. The McCormick et al. patent discloses the use of flexible loop-like straps for limiting the distal movement of a tip guard.

Needle shields that incorporate movable tip guards are typically manually actuated. For example, U.S. Pat. Nos. RE36,447 and RE36,398, both to Byrne et al., disclose a safety device for a hypodermic needle that includes a plastic sheath, which is used to cover the puncture tip of the needle. The plastic sheath incorporates a thumb guard, which the user of the safety device may grasp to move the plastic sheath to a position covering the puncture tip of the needle. U.S. Pat. No. 5,951,525 to Thome et al. discloses a manually operated safety needle apparatus that includes two pairs of opposed legs adapted to move the tip guard of the apparatus to a position covering the used needle cannula. U.S. Pat. Nos. 5,562,637 and 5,562,636, both to Utterberg, disclose a rectangular needle protector sheath for use with a needle cannula that may be extended over the needle cannula after it is used. Other prior art devices, such as those disclosed by U.S. Pat. No. 5,290,264 to Utterberg and U.S. Pat. No. 5,192,275 to Burns, provide "grippable" members attached to the tip guards to facilitate moving the tip guards to a position covering the puncture tip of a needle cannula.

Conventional tip guards, such as those discussed hereinabove, often require extensive mechanics for positioning the tip guard over the needle cannula. This results in complex arrangements that are costly to manufacture and assemble. Additionally, operation of the needle assemblies to move the tip guard into the proper position over the pointed distal end of the needle cannula requires substantial manual manipulation by the user of the device, exposing the user to potential needle-stick wounds.

Needle assemblies may also incorporate passively activated safety features. In such devices, the needle shielding feature is passively actuated upon normal usage of the device. For example, the activation of the safety feature may automatically occur, such as upon removing a safety cover and after releasing the device after insertion of the needle into the patient's injection site. The safety feature may be a safety shield that is propelled toward the needle tip, or a force that is exerted on the needle to retract the needle into the body of the device. U.S. Patent Application Publication No. 2002/0099339 to Niermann discloses a passive safety blood collection set which includes a tip guard slidably movable along a needle cannula. The tip guard is mounted to a needle hub through a pair of collapsible leaves, which are collapsed onto themselves and held in place by a packaging cover. In use, the practitioner holds the leaves in the collapsed or folded state to remove the cover, and then releases the leaves enabling them to unfold to propel the tip guard distally.

SUMMARY OF THE INVENTION

A need exists for a blood collection set including a shielding needle assembly that achieves secure and effective shielding of a used needle cannula, and which is simple and inexpensive to manufacture and easy to operate. An additional need exists for a blood collection set with a passively operated shielding mechanism that allows a healthcare professional to probe for a vein without activating the shielding mechanism.

A needle assembly is provided including a hub or a housing with a passageway extending therethrough and a needle cannula having a puncture tip extending from a forward end of the housing. A shielding member is movable between a first position in which the puncture tip of the needle cannula is exposed and a second position in which the puncture tip of the needle cannula is shielded by the shielding member. The shielding member is maintained in the first position against a biasing force provided by a drive member, which biases the shielding member toward the second position. An activation material is associated with the shielding member and is adapted to deform upon flow of fluid through the passageway of the housing. Fluid flowing through passageway of the housing causes the activation material to deform, thereby releasing the shielding member from the first position and causing the drive member to bias the shielding member toward the second position.

The needle assembly may include an interference engagement between the shielding member and the housing that maintains the shielding member in the first position against the biasing force. Capillary passages or tubes may also be disposed within the passageway of the housing and in fluid communication with the needle cannula for diverting a fluid from the needle cannula to the activation material. In one embodiment, the deformation of the activation material, such as expansion thereof, may force an actuator to contact the shielding member to release it from the first position. Deformation of the activation material may alternatively occur due to a temperature change caused by fluid flowing through the passageway of the housing, such as blood at physiologic temperature.

According to another embodiment, a shielding needle assembly includes a needle cannula having a proximal end and a distal end with a puncture tip; a needle hub having a proximal end and a distal end and a passage between the ends, with an interior portion of the needle hub distal end supporting the needle cannula proximal end; a shielding member movable between a first position in which the puncture tip of the needle cannula is exposed from the shielding member and a second position in which the puncture tip of the needle cannula is within the shielding member; a drive member biasing the shielding member toward the second position; and an activation material adapted to deform upon contact with a fluid medium flowing through the needle cannula. The shielding member and the needle hub include an interference engagement therebetween for maintaining the shielding member in the first position against a biasing force of the drive member. A fluid medium flowing through the needle cannula causes the activation material to deform and release the interference engagement between the shielding member and the needle hub and allowing the drive member to bias the shielding member toward the second position.

In one particular embodiment, a blood collection set is provided which comprises such a shielding needle assembly with a flexible tube extending from the needle hub or housing. The flexible tube may include a fixture, or may otherwise be adapted to engage with a non-patient needle cannula at an opposed end of the tube, for connection with a receptacle for blood collection.

A further embodiment involves a method of actuating a shielding needle assembly. The method includes the steps of providing a shielding needle assembly comprising a housing including a passageway extending therethrough and a needle cannula having a puncture tip extending from a forward end thereof. The assembly further includes a shielding member biased toward a second position in which the puncture tip of the needle cannula is encompassed within the shielding member, and maintained against such bias in a first position in which the puncture tip of the needle cannula is exposed from the shielding member. In the method, the puncture tip of the needle cannula is inserted through the skin of a patient to allow a fluid medium to flow through the needle cannula, such as blood obtained from the patient during a blood collection procedure. Such fluid flow through the needle cannula causes the shield member to be released from the first position.

For example, the assembly may include an activation material associated with an interference engagement between the shielding member and the housing. Fluid flow through the needle cannula may cause the activation material to deform, thereby releasing the interference engagement between the shielding member and the housing and allowing the shielding member to be biased toward the second position. In one embodiment, a portion of the fluid medium may be diverted from the cannula to the fluid activated material, such as through one or more capillary passages, to cause the material to deform.

In a further embodiment, the method may further comprise a step of removing the puncture tip of the needle cannula from a patient, allowing the shield member to be biased to the second position to cover the puncture tip of the needle cannula. Moreover, while the fluid flow through the needle cannula may be blood from the patient such as during a blood collection procedure, it is contemplated that the fluid flow could be any bodily fluid removed from a patient, as well as fluid medium being transfused into a patient, such as blood, intravenous drug mediums, and the like.

Further details and advantages of the present invention will become apparent upon reading the following detailed description in conjunction with the accompanying drawings, wherein like reference numerals identify like parts throughout.

BRIEF DESCRIPTION OF THE DRAWINGS

FIG. 7 is a longitudinal cross-sectional view of an alternate embodiment of the shielding needle assembly; and FIG. 8 is a perspective view of an actuator mechanism of the shielding needle assembly of FIG. 7 enlarged for magnification purposes.

DETAILED DESCRIPTION OF THE PRESENT INVENTION

Figure 1:
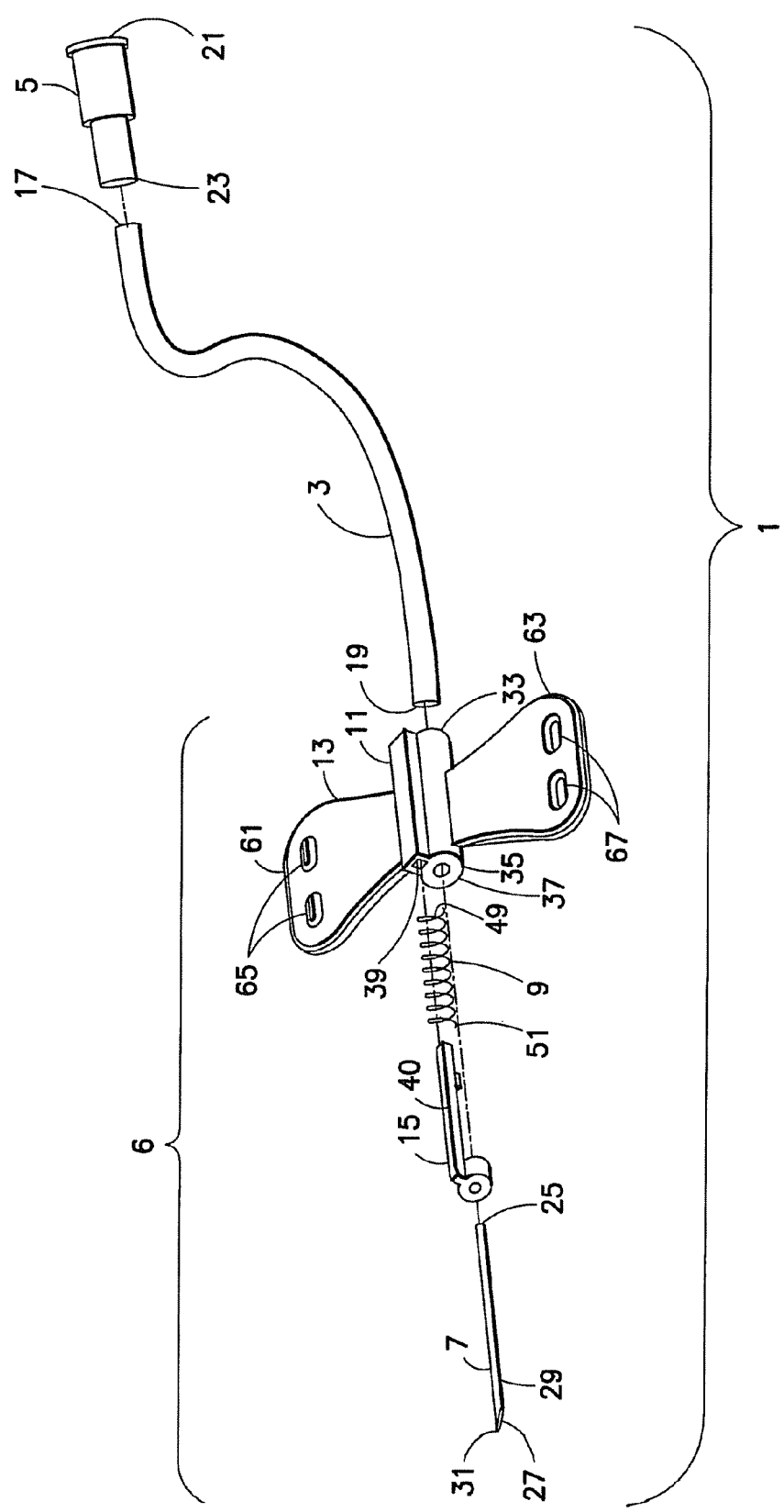
FIG. 1 is an exploded perspective view of a blood collection set in accordance with an embodiment of the present invention.

For purposes of the description hereinafter, the words "upper", "lower", "right", "left", "vertical", "horizontal", "top", "bottom", "lateral", "longitudinal" and like spatial terms, if used, shall relate to the described embodiments as oriented in the drawing figures. However, it is to be understood that many alternative variations and embodiments may be assumed except where expressly specified to the contrary. It is also to be understood that the specific devices and embodiments illustrated in the accompanying drawings and described herein are simply exemplary embodiments of the invention.

Generally, an embodiment of the invention relates to a passively activated shieldable needle assembly. Passive activation of the safety features of the present device is accomplished during normal operation of the assembly in connection with a standard medical procedure, without the need for any other conscious action by the health care professional. The shielding feature of the assembly does not activate until use of the device in connection with a patient, such as upon fluid flow, i.e., blood flow, through the needle cannula, after venipuncture. Accordingly, an embodiment involves activation of the shielding feature upon flashback. The advantage of this type of arrangement is the automation as to when the shielding member activates. For example, a healthcare professional does not always enter the targeted blood vessel during the first venipuncture attempt. The passively activated assembly disclosed herein allows the healthcare professional to stick the patient with a needle cannula and then probe for a vein without activation of the shielding member. Embodiments of the present invention generally include a shielding needle assembly for use in a fluid collection or infusion assembly, and encompasses the needle assembly itself as well as such a fluid collection or infusion assembly, for example, a blood collection set.

Figure 2:
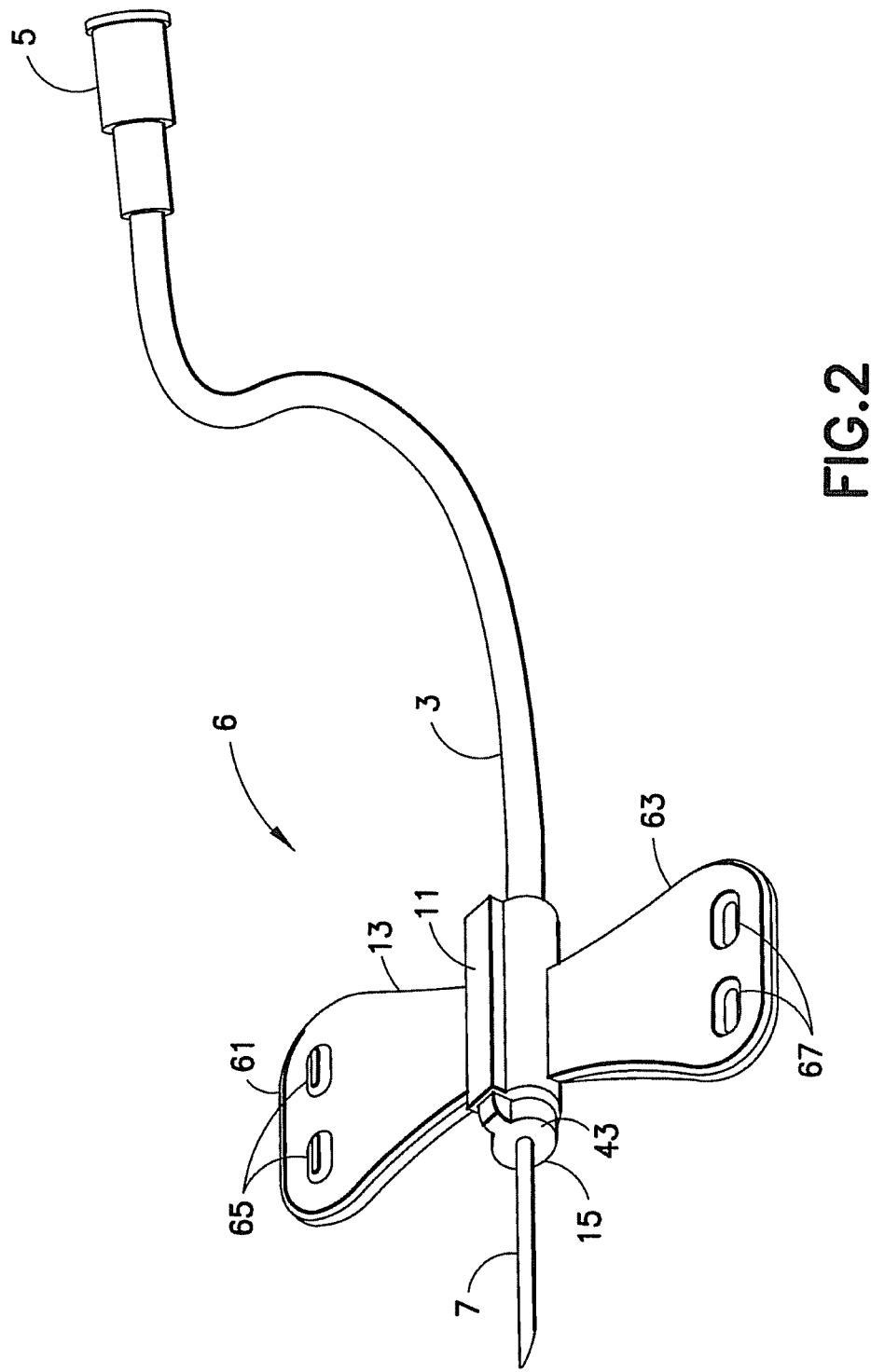
FIG. 2 is a perspective view of the blood collection set of FIG. 1 in an assembled condition.

With reference to FIGS. 1 and 2, a fluid collection/infusion set 1 includes a safety shielding needle device or assembly 6, with flexible tubing 3 extending from the needle device or assembly 6. A protective cap or shield such as a packaging cover (not shown) may be removably mounted to the needle assembly 6 opposite flexible tubing 3, such as through frictional engagement therewith for protection during delivery and storage. A first end or proximal end 17 of flexible tubing 3 is adapted for connection with a receptacle such as for blood collection, while needle assembly 6 extends from a second end or distal end 19 of flexible tubing 3.

Tubing 3 includes proximal end 17, distal end 19, and a passage extending between the ends. Tubing 3 may be conventional intravenous tubing used in conventional blood collection sets. Proximal fitting 5 is molded unitarily from a plastic material and includes a proximal end 21, a distal end 23 and a passage extending between the ends. Portions of the passage adjacent distal end 23 are configured to telescope tightly within or over proximal end 17 of tubing 3 so that the passage through tubing 3 communicates with the passage through proximal fitting 5. Proximal end 21 of fitting 5 may define a female luer connector that can be mated with an appropriate male luer connector to infuse a medication into a patient. For example, a male luer connector at the distal end of a conventional syringe may be connected directly to proximal fitting 5 for infusing a medication into the patient. In this instance, a separate male luer cap can be provided for closing proximal fitting 5. Alternatively, fitting 5 may be adapted to accommodate a non-patient needle assembly including an elastomeric sheath, such as through a male luer connector hub engaged with fitting 5, as is known in the art. In such an embodiment, a conventional needle holder may be fitted with the non-patient needle assembly so as to be placed in communication with an evacuated blood collection tube, thereby providing a blood collection assembly in known manner. Other fittings may be threadedly engaged with proximal fitting 5 in accordance with the specific intended use of collection/infusion set 1. Additionally, connectors of other configurations may be employed to achieve a particular objective.

As noted, blood collection set 1 includes a needle device or assembly 6 extending from flexible tubing 3. With general reference to FIGS. 1 and 2, one embodiment of the invention defines the shielding needle assembly 6 generally including a needle cannula 7 in connection with a needle housing or hub 11 having and a winged structure 13, a safety shielding member 15 for protectively shielding the puncture tip of the needle cannula 7 after use, and a drive member 9 for moving the needle portion and the shield member with respect to each other.

Needle cannula 7 includes a proximal end 25 and an opposing distal end 27, with a lumen 29 extending through needle cannula 7 from the proximal end 25 to the distal end 27. The distal end 27 of needle cannula 7 is beveled to define a sharp puncture tip 31, such as an intravenous puncture tip. The puncture tip 31 is provided for insertion into a patient's blood vessel, such as a vein, and is therefore designed to provide ease of insertion and minimal discomfort during venipuncture.

Figure 3:
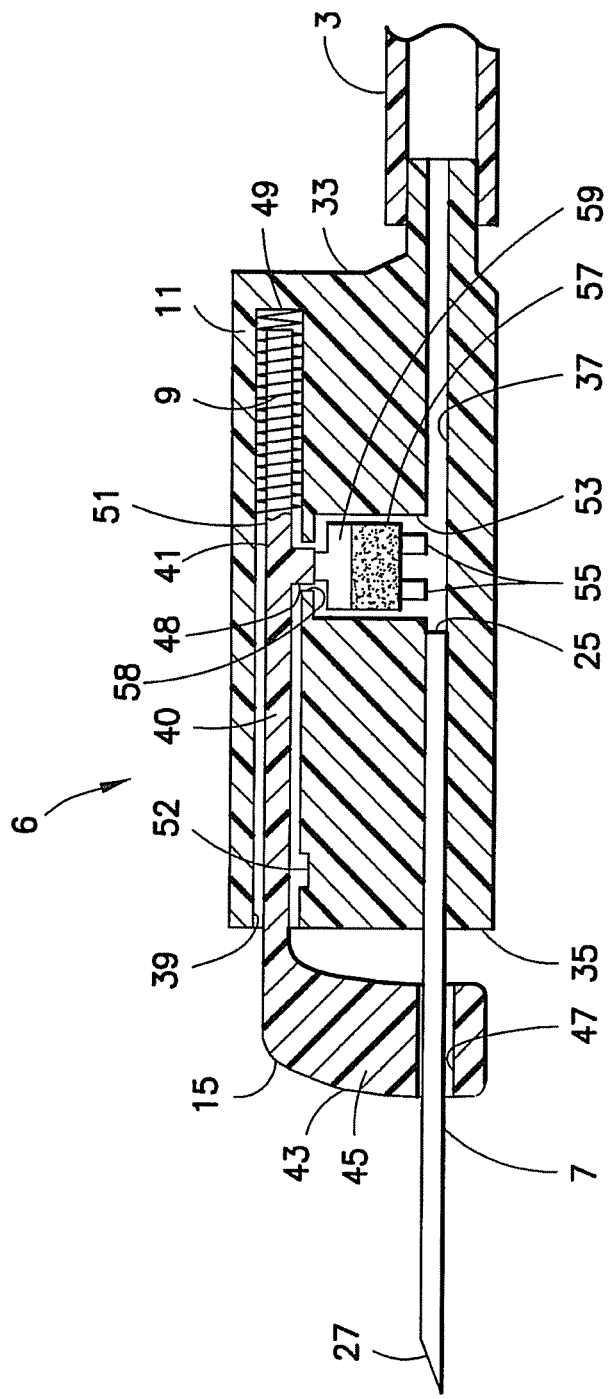
FIG. 3 is a longitudinal cross-sectional view of the shielding needle assembly depicted in the blood collection set of FIG. 1.

With reference to FIG. 3, and with continuing reference to FIGS. 1 and 2, needle hub 11 is generally tubular or cylindrical in shape and includes a proximal end 33, a distal end 35, and a first passage 37 extending between the ends. Portions of first passage 37 adjacent proximal end 33 of needle hub 11 are dimensioned to receive distal end 19 of tubing 3. Portions of first passage 37 adjacent distal end 35 of needle hub 11 are dimensioned for slidable receipt of proximal end 25 of needle cannula 7. Needle hub 11 may be molded from a plastic material such as polycarbonate, polypropylene, polyethylene, acrylic, polystyrene, and ABS. Further, needle hub 11 may be molded from a transparent or translucent material to enable observation of blood or other fluid flowing through needle hub 11. Needle cannula 7 may be fixedly attached and secured to needle hub 11 through an appropriate medical grade adhesive, for example, epoxy and the like.

Figure 4:
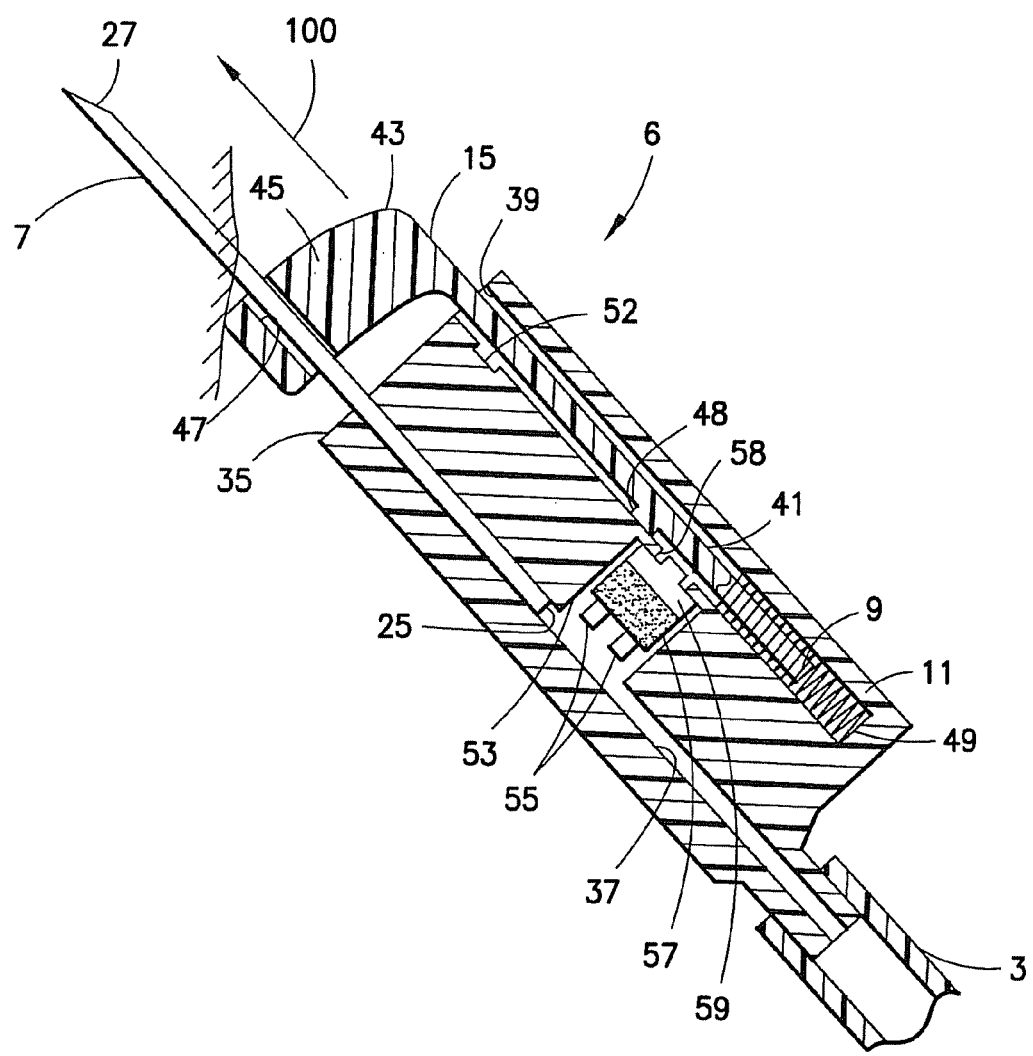
FIG. 4 is a cross-sectional view of the shielding needle assembly during use with a needle cannula piercing a patient's skin.

Needle assembly 6 further includes shielding member 15. Shielding member 15 is desirably a unitary structure, which may be molded from a plastic material. Shielding member 15 includes a proximal end 41 and a distal end 43. At least a portion of shielding member 15 is in telescoping association with needle hub 11. In particular, shielding member 15 is axially movable with respect to a longitudinal axis defining needle assembly 6 between a first retracted position in which puncture tip 31 of needle cannula 7 is exposed from the distal end 43 of shielding member 15, as shown in FIG. 2, and a second extended position in which puncture tip 31 of needle cannula 7 is encompassed within the distal end 43 of shielding member 15, as shown in FIG. 4. This may be accomplished by providing a portion of shielding member 15 in slidable engagement with needle hub 11.

For example, shielding member 15 may include a portion such as extension member 40 extending toward proximal end 41 thereof which extends within a portion of needle hub 11 for slidable engagement therewith. In this manner, needle hub 11 may include a second passage 39, which may be distinct from first passage 37 and positioned substantially parallel therewith. Second passage 39 defines an opening through the housing of needle hub 11 for accommodating extension member 40 of shielding member 15. Moreover, distal end 43 of shielding member 15 may comprise a shielding portion 45 that defines a central opening 47 through which the needle cannula 7 extends. Central opening 47 permits shielding member 15 to move along the needle cannula 7 between the retracted and extended positions, as will be discussed in more detail herein.

As noted, shielding member 15 is axially movable with respect to needle hub 11. The needle assembly 6 further includes a drive member 9 extending between the needle hub 11 and the shielding member 15, providing a biasing force to bias the shielding member 15 axially or longitudinally away from needle hub 27. Drive member 9 may be in the form of a coil or compression spring or like biasing element and is generally adapted to move shielding member 15 from the retracted position to the extended position. The drive member 9 has a proximal end 49 and a distal end 51. The proximal end 49 is generally disposed in the housing defined by second passage 39 near proximal end 33 of needle hub 11. Distal end 51 is generally in contact with proximal end 41 of shielding member 15. The engagement of distal end 51 of the drive member 9 with proximal end 41 of shielding member 15 forms the physical interface between drive member 9 and shielding member 15 for moving shielding member 15 from the retracted position to the extended position.

In a general sense, shield member 15 is maintained from movement with respect to needle hub 11 against the biasing force of drive member 9 to maintain needle assembly 6 in the first position with puncture tip 31 extending through the forward end of shielding member 15 at a sufficient distance to permit venipuncture. Shielding member 15 may be maintained or held in this retracted position with respect to needle hub 11 through a releasable engagement adapted to maintain the shielding member 15 in position against the biasing force of drive member 9. For example, shielding member 15 and needle hub 11 may include interengaging structure which provides an interference engagement therebetween to prevent the drive member 9 from biasing the shielding member 15 away from the needle hub 11 in a longitudinal direction. In particular, proximal end 41 of shielding member 15 may be configured to include an engagement member 48 for interference engagement with a corresponding portion of needle hub 11, such as shoulder 58. This interference engagement between engagement member 48 and shoulder 58 provides a mechanism to maintain shielding member 15 in the retracted position against the biasing force of drive member 9 until release of the interference engagement therebetween.

The shielding feature of needle assembly 6 is accomplished upon fluid flow through needle cannula 7, such as during a blood collection procedure. Accordingly, needle assembly 6 further includes a mechanism to effect actuation of the shielding feature upon fluid flow therethrough. In one embodiment of the present invention, this is accomplished by effecting release of the interference engagement between engagement member 48 and shoulder 58. For example, needle assembly 6 further includes structure which is activated upon fluid flow through needle cannula 7. As depicted in FIG. 3, needle assembly 6 includes an activation material 57 within the interior passageway defined by the structure of needle hub 11. Activation material 57 is a material which is adapted to deform, i.e., adapted to expand, contract, dislocate, or otherwise change in dimension, when a fluid is disposed within needle hub 11 of needle assembly 6, such as when the internal environment within needle hub 11 is exposed to a fluid or when activation material 57 is directly contacted with a liquid.

Desirably, activation material 57 is a material which is capable of deforming, i.e., changing size or shape, such as expanding in size and/or shape, upon contact with a liquid, such as blood. This deformation may be accomplished by a physical expansion of the activation material 57, such as upon contact with blood flow through needle hub 11, causing activation material 57 to absorb a portion of the blood and physically expand. Non-limiting examples of useful materials include highly compressed materials such as compressed sponges, hydrogels, expandable foams, expandable powders, and the like.

Further, activation material 57 may be deformed by exposing activation material 57 to a certain temperature range or exposing activation material 57 to a temperature change. This temperature range or temperature change may be caused by the reception of fluid, such as blood, within the interior passageway defined by the structure of needle hub 11. This may be desirably accomplished by providing activation material 57 as a material that is deformable upon exposure to a temperature range consistent with a patient, such as a patient-derived heat, based upon use of the device with a patient. For example, upon use of the device in a sampling procedure, the temperature of in vivo blood from the patient passing through the device causes the activation material 57 to be exposed to the temperature range of the patient's blood. Such exposure may involve direct contact of the patient's blood with the activation material 57, or merely a change in the temperature of the environment surrounding the activation material 57, thereby exposing the activation material to such a change in temperature. The activation material 57 may thermally expand based upon contact with the fluid itself or based on the environment having a temperature change. Non-limiting examples of useful materials adapted for deformation upon a change in temperature may include shape memory materials such as shape memory alloys including copper-zinc-aluminum-nickel alloys, copper-aluminum-nickel alloys, and nickel-titanium (NiTi) alloys. In such embodiments, the activation material 57 may form part or all of actuator 59, such that the change in shape of the activation material/actuator 57, 59 causes release of the interference engagement holding the shielding member 15 in a shielding position.

Activation material 57 may be positioned within needle assembly 6 so as to be in fluid contact with needle cannula 7. Needle hub 11 may further include a third passage 53 extending therein in a manner connecting first passage 37 and second passage 39, desirably substantially perpendicular to first passage 37. Third passage 53 houses activation material 57 therein, and may further be configured to house a series of passageways such as capillary tubes 55, positioned adjacent to activation material 57. Shoulder 58 may represent an endwall portion of third passage 53, whereby third passage 53 is configured to provide for the interference engagement between shielding member 15 and needle hub 11 for maintaining shielding member 15 in the retracted position against the bias of drive member 18. Moreover, an actuator 59 may also be positioned within third passage 53 adjacent activation material 57. Actuator 59 is adapted to move upon activation of activation material 57. Accordingly, actuator 59 is desirably in fixed relation with activation material 57, and may therefore be affixed thereto or form a portion thereof. As will be discussed in further detail, movement of activation material 57 upon contact with fluid or exposure to a temperature change causes corresponding movement of actuator 59, which in turn releases the interference engagement between shielding member 15 and needle hub 11.

Needle assembly 6 may further include a mechanism or structure for preventing a return movement of shielding member 15 with respect to needle hub 11 from the extended position to the retracted position after activation thereof. For example, a second interference engagement mechanism may be provided between shielding member 15 and needle hub 11. Second passage 39 may further include a stop member 52 in the regard, designed to interact with engagement member 48 of shielding member 15 to secure shielding member 15 in the extended position. In addition to or instead of such engagement, shielding member 15 may further include a protective clip for locking out puncture tip 31 of needle cannula 7 and preventing re-exposure thereof. Such a clip is known in the art, for example, as shown in U.S. Patent Application Publication No. US2005/0119627, the disclosure of which is incorporated herein by reference. In this manner, the distal end 43 of shielding member 15 effectively functions as a type of tip guard.

Needle hub 11 may further include a winged structure 13. Winged structure 13 may be molded unitarily from an elastic material such as polyolefin, polyvinyl chloride, or other such elastomeric polymers or may be molded integrally with needle hub 11. Winged structure 13 includes flexible side panels 61 and 63. Panels 61 and 63 are molded with a top surface that is relatively smooth. However, the top surface of panel 61 includes a pair of arcuate projections 65. The top surface of panel 63 includes a pair of arcuate recesses 67 that are dimensioned, disposed, and configured to receive projections 65 on panel 61 when panels 61 and 63 are folded so that the top surfaces thereof are in face-to-face engagement with one another. The interengagement of projections 65 with recesses 67 ensures that folded panels 61 and 63 function as a handle without slipping relative to one another. The bottom surfaces of panels 61 and 63 may be provided with a plurality of tactile bumps (not shown). The tactile bumps facilitate gripping of folded panels 61 and 63 between a thumb and forefinger of the user. The color of the winged structure 13 may designate the gauge of the needle cannula 7. Alternate embodiments where winged structure 13 has only one side panel 61 or 63 are contemplated to provide an alternate means to manipulate the needle assembly by the user.

Figure 5:
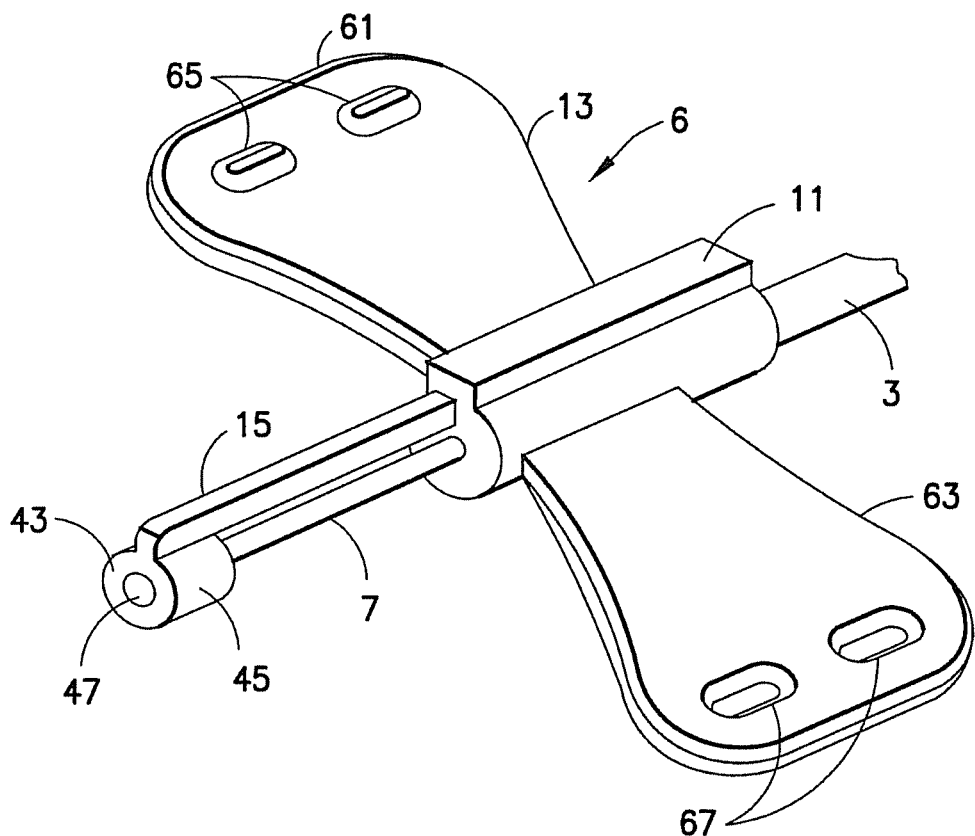
FIG. 5 is a perspective view of the shielding needle assembly with a shielding member in an extended position.
Figure 6:
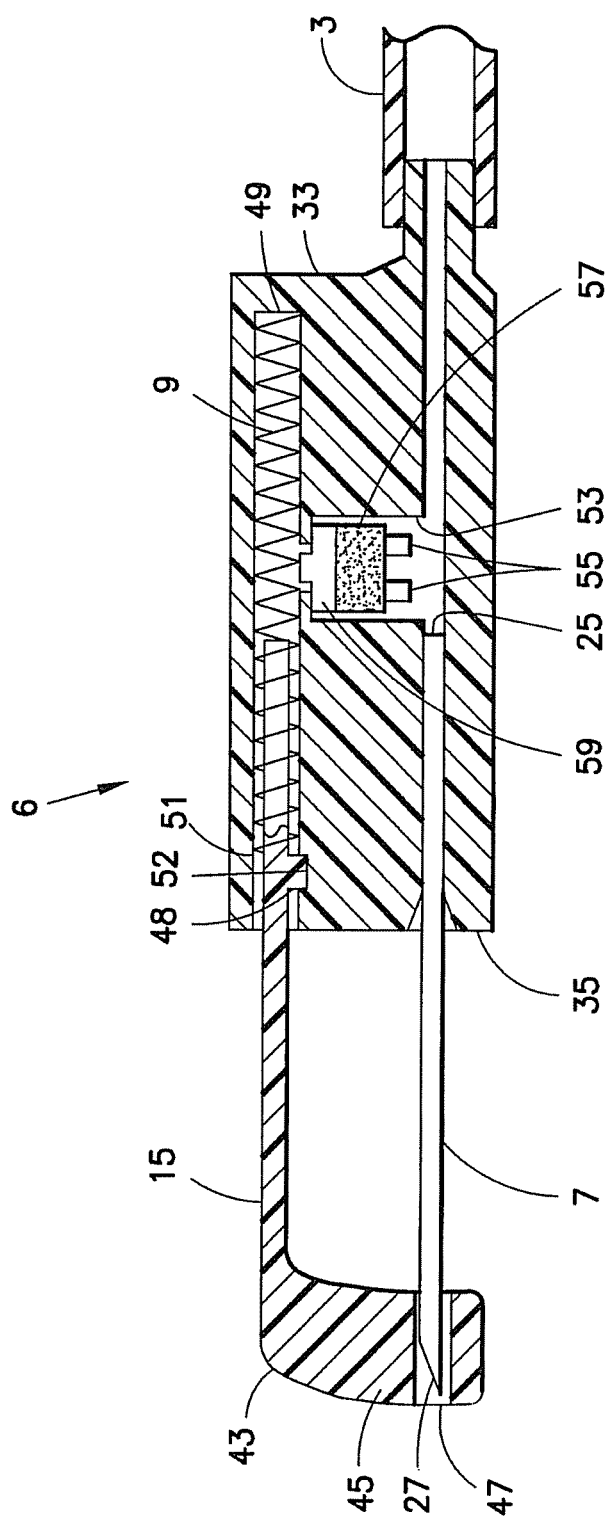
FIG. 6 is a cross-sectional view of the shielding needle assembly of FIG. 5.

With reference to FIGS. 4-6, and with continuing reference to FIGS. 1-3, blood collection set 1 is used by folding panels 61 and 63 of winged structure 13 toward one another and into face-to-face engagement so that projections 65 on upper surface of panel 61 are received in recesses 67 on the upper surface on panel 61 to prevent shifting of panels 61 and 63. The tactile bumps (not shown) on the bottom surfaces of panels 61 and 63 can then be held securely in face-to-face engagement between a thumb and forefinger. Any packaging cover or protective cover can then be removed from needle assembly 6.

A healthcare professional then guides puncture tip 31 of needle cannula 7 into a targeted location on the patient and employs proximal fitting 5 at proximal end 17 of tubing 3 for connection to an evacuated container or a source of fluid that will be infused into the patient. As venipuncture is achieved, blood flows into and through needle cannula 7. A portion of the blood flow is diverted via capillary tubes 55 through third passage 53. The diverted blood contacts activation material 57 causing it to expand. This expansion forces actuator 59 to displace engagement member 48 from its interference engagement with shoulder 58 within third passage 53. Drive member 9 is then free to propel shielding member 15 out of the retracted position toward the extended position distally along needle cannula 7 in an axial direction designated by arrow 100 in FIG. 4, with shielding portion 45 of shielding member 15 sliding or gliding along needle cannula 7 toward distal end 27 of needle cannula 7.

During an actual blood collection procedure, the distal movement of shielding member 15 will terminate when the distal end 43 of shielding member 15 contacts the skin of the patient, as shown in FIG. 4. Drive member 9 still exerts a distally-directed biasing force on shielding member 15, but this force is resolved by the frictional force that acts on the needle cannula 7 as a result of being in the blood vessel of the patient. The healthcare professional may then proceed to complete the blood collection procedure, for example, using evacuated blood collection tubes or a syringe. The healthcare professional then proceeds to remove the blood collection set 1 from the blood vessel of the patient. As needle cannula 7 is removed from the blood vessel of the patient, shielding member 15 is urged by drive member 9 to move closer to distal end 27 of the needle cannula 7. As needle cannula 7 is fully removed from the patient's blood vessel, shielding portion 45 of shielding member 15 is urged by drive member 9 to fully encompass needle cannula 7, as generally depicted in FIGS. 5 and 6. Stop member 52 in second passage 39 interacts with engagement member 48 of shielding member 15 to secure shielding member 15 in this fully extended position.

With reference to FIGS. 7 and 8, an alternate embodiment of the shielding needle assembly employing a different type of actuator mechanism. The alternate embodiment of a shielding needle assembly 101 includes a needle cannula 103, a drive member 105, a needle hub 107, and a shielding member 109.

Needle cannula 103 includes a proximal end 111 and an opposing distal end 113, with a lumen extending through needle cannula 103 from proximal end 111 to distal end 113. Distal end 113 of needle cannula 103 is beveled to define a sharp puncture tip 115, such as an intravenous puncture tip. The puncture tip 115 is provided for insertion into a patient's blood vessel, such as a vein, and is therefore designed to provide ease of insertion and minimal discomfort during venipuncture.

Needle hub 107 is generally tubular or cylindrical in shape and includes a proximal end 117, a distal end 119 and at least a first passage 121 and a second passage 123 extending between the ends. First passage 121 and second passage 123 are positioned substantially parallel to each other. Portions of first passage 121 adjacent proximal end 117 of needle hub 107 are dimensioned to receive an end of a flexible tubing 125. Portions of first passage 121 adjacent distal end 119 of needle hub 107 are dimensioned for slidable receipt of proximal end 111 of needle cannula 103, with needle cannula 103 fixedly attached and secured therein in known manner.

Second passage 123 defines a housing for drive member 105 and shielding member 109. Shielding member 109 is a unitary structure, desirably molded from a thermoplastic material, and includes a proximal end 127 and a distal end 128. Shielding member also includes a shielding portion 131 that defines a central opening 132 through which the needle cannula 103 extends and a support portion 133. Central opening 132 permits shielding member 109 to move along the needle cannula 103 between the retracted and extended positions. Support portion 133 is divided into a first portion 135 and a second portion 137. First portion 135 has a diameter that is smaller than the diameter of second portion 137. Drive member 105 may be in the form of a coil compression spring or like biasing element and is generally adapted to move shielding member 109 from the retracted position to the extended position. The drive member 105 has a proximal end 139 and a distal end 141. The proximal end 139 is generally disposed in the housing defined by second passage 123 near proximal end 117 of needle hub 107. Distal end 141 is generally in contact with proximal end 127 of shielding member 109. The engagement of distal end 141 of the drive member 105 with proximal end 127 of shielding member 109 forms the physical interface between drive member 105 and shielding member 109 for moving shielding member 109 from the retracted position to the extended position. Second passage 123 further includes a lock arrangement 143 designed to maintain shielding member 109 in a retracted position against the biasing force of drive member 105 biasing shielding member 109 toward the extended position. Lock arrangement 143 includes a body portion 145 with an opening 147 therein, defining a key-slot type arrangement. Opening 147 prevents second portion 137 of support portion 133 of shielding member 109 to pass therethrough when body portion 145 is in a first position, and allows second portion 137 of support portion 133 of shielding member 109 to pass therethrough when in body portion 145 is in a second position. Second passage 123 includes a stop member 150 designed to interact with second portion 137 of support portion 133 of shielding member 109 to secure shielding member 109 in the extended position.

Needle hub 107 further includes a third passage 149 connecting first passage 121 and second passage 123. Third passage 149 houses a series of capillary tubes 151, activation material 153 positioned adjacent to capillary tubes 151, and an actuator 155 positioned adjacent to activation material 153 and in contact with lock arrangement 143.

Shielding needle assembly 101 is used by guiding puncture tip 115 of needle cannula 103 into a targeted location on a patient. As blood flows through needle cannula 103, some of the blood flow is diverted via capillary tubes 151 through third passage 149. The diverted blood causes activation material 153 to expand. This expansion forces actuator 155 to displace body portion 145 of lock arrangement 143 from a first position, where second portion 137 of support portion 133 of shielding member 109 is prevented from passing therethrough, to a second position, where second portion 137 of support portion 133 of shielding member 109 is free to pass therethrough. Drive member 105 then propels shielding member 109 distally along needle cannula 103 in an axial direction, with shielding portion 131 of shielding member 109 sliding or gliding along needle cannula 103 toward distal end 113 of needle cannula 103.

During an actual blood collection procedure, the distal movement of shielding member 109 will terminate when the distal end 129 of shielding member 109 contacts the skin of the patient. Drive member 105 still exerts a distally-directed biasing force on shielding member 109, but this force is resolved by the frictional force that acts on the needle cannula 103 as a result of being in the blood vessel of the patient. The healthcare professional may then proceed to complete the blood collection procedure, for example, using evacuated blood collection tubes or a syringe. The healthcare professional then proceeds to remove the needle assembly 101 from the blood vessel of the patient. As needle cannula 103 is removed from the blood vessel of the patient, shielding member 109 is urged by drive member 105 to move closer to distal end 113 of the needle cannula 103. As needle cannula 103 is fully removed from the patient's blood vessel, shielding portion 131 of shielding member 109 is urged by drive member 105 to fully encompass puncture tip 115 of needle cannula 103. Stop member 150 in second passage 123 interacts with second portion 137 of support portion 133 of shielding member 109 to secure shielding member 109 in the extended position.

Additionally, as mentioned hereinabove, activation material 57 or 153 may also be deformed by exposing activation material 57 or 153 to a certain temperature range or exposing activation material 57 or 153 to a temperature change. This temperature range or temperature change may be caused by the reception of fluid, such as blood, within the interior passageway defined by the structure of needle hub 11. The temperature change causes activation material 57 or 153 to expand. This expansion displaces actuator 59 or 155 thereby releasing shielding member 15 or 109 as discussed hereinabove.

While the needle assembly has been described in terms of embodiments for use in connection with a blood collection system, it is further contemplated that the needle assembly could be used with other medical procedures, such as in conjunction with a conventional intravenous infusion set, which are well-known in the art for use with needle assemblies. While various embodiments in many different forms are shown in the drawings and described herein in detail as exemplary embodiments of the invention, the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

The invention claimed is:

1. A needle assembly, comprising:
a housing including a passageway extending therethrough and a needle cannula having a proximal end located within the passageway and a puncture tip extending from a forward end thereof;
a shielding member movable with respect to the housing between a first position in which the puncture tip of the needle cannula is exposed and a second position in which the puncture tip of the needle cannula is shielded by the shielding member, the shielding member maintained in the first position against a biasing force provided by a drive member biasing the shielding member toward the second position; and
an activation material located within the passageway and associated with the shielding member, the activation material being adapted to expand, contract, or otherwise change in dimension upon direct contact with a fluid flowing through the passageway of the housing, wherein the fluid flows into and through the needle cannula and the fluid is then diverted to the passageway where the fluid contacts the activation material,
wherein the fluid flowing through the passageway of the housing causes the activation material to expand, contract, or otherwise change in dimension, thereby releasing the shielding member from the first position and causing the drive member to bias the shielding member toward the second position. The needle assembly further comprising capillary tubes disposed within the passageway of the housing and in fluid communication with the needle cannula for diverting the fluid from the needle cannula to the activation material.

2. The needle assembly of claim 1, further comprising an interference engagement between the shielding member and the housing maintaining the shielding member in the first position against the biasing force.

3. The needle assembly of claim 1, wherein the drive member comprises a coil spring.

4. The needle assembly of claim 1, wherein the activation material comprises a material selected from the group consisting of hydrogels, compressed sponges, expandable foams, expandable powders, and combinations thereof.

5. The needle assembly of claim 1, wherein the expansion, the contraction, or the otherwise change in dimension of the activation material forces an actuator to release the shielding member from the first position.

6. A needle assembly comprising:
a housing including a passageway extending therethrough and a needle cannula having a puncture tip extending from a forward end thereof;
a shielding member movable with respect to the housing between a first position in which the puncture tip of the needle cannula is exposed and a second position in which the puncture tip of the needle cannula is shielded by the shielding member, the shielding member maintained in the first position against a biasing force provided by a drive member biasing the shielding member toward the second position;

an activation material associated with the shielding member and adapted to deform upon a flow of a fluid through the passageway of the housing; and capillary tubes disposed within the passageway of the housing and in fluid communication with the needle cannula for diverting the fluid from the needle cannula to the activation material, wherein the fluid flowing through the passageway of the housing causes the activation material to deform, thereby releasing the shielding member from the first position and causing the drive member to bias the shielding member toward the second position.

7. A shielding needle assembly comprising:

a needle cannula having a proximal end and a distal end with a puncture tip;

a needle hub having a proximal end and a distal end and a passage between the proximal and distal ends of the needle hub, with an interior portion of the needle hub distal end supporting the needle cannula proximal end;

a shielding member movable between a first position in which the puncture tip of the needle cannula is exposed and a second position in which the puncture tip of the needle cannula is shielded by the shielding member;

a drive member biasing the shielding member toward the second position, the shielding member and the needle hub including an interference engagement therebetween for maintaining the shielding member in the first position against a biasing force of the drive member; and an activation material located within the passage, the activation material adapted to expand, contract, or otherwise change in dimension upon direct contact with a fluid medium flowing through the needle cannula, wherein the fluid medium flows into and through the needle cannula and the fluid medium is then diverted to the passage where the fluid medium contacts the activation material thereby causing the activation material to expand, contract, or otherwise change in dimension and release the interference engagement between the shielding member and the needle hub and allowing the drive member to bias the shielding member toward the second position, the shielding needle assembly further comprising capillary tubes disposed within the passage of the needle hub and in fluid communication with the needle cannula for diverting the fluid medium from the needle cannula to the activation material.

8. The shielding needle assembly of claim 7, wherein the drive member comprises a coil spring.

9. The shielding needle assembly of claim 7, wherein the activation material comprises a material selected from the group consisting of hydrogels, compressed sponges, expandable foams, expandable powders, and combinations thereof.

10. The shielding needle assembly of claim 7, wherein the expansion, the contraction, or the otherwise change in dimension of the activation material causes movement of an actuator which releases the interference engagement between the shielding member and the needle hub.

11. The shielding needle assembly of claim 7, wherein the interference engagement between the shielding member and the needle hub comprises a finger at a rearward end of the shielding member extending within a recess of the needle hub, and wherein the expansion of the activation material releases the finger out of the recess.

12. The shielding needle assembly of claim 11, wherein the expansion of the activation material causes movement of an actuator which contacts the finger of the shielding member to release the finger out of the recess of the needle hub.

13. A blood collection set comprising the shielding needle assembly of claim 7 including a flexible tube extending from the needle hub, the flexible tube comprising a non-patient needle cannula at an opposed end adapted for connection to a receptacle for blood collection.

14. A method of actuating a shielding needle assembly comprising:

providing the shielding needle assembly comprising a housing including a passageway extending therethrough; a needle cannula having a proximal end located within the passageway and a puncture tip extending from a forward end thereof and a shielding member in a first position biased toward a second position in which the puncture tip of the needle cannula is shielded by the shielding member, the shielding member maintained against the bias in the first position in which the puncture tip of the needle cannula is exposed; and an activation material located within the passageway and associated with the shielding member, the activation material adapted to expand, contract, or otherwise change in dimension upon direct contact with a fluid medium flowing through the needle cannula, wherein the fluid medium flows into and through the needle cannula and the fluid medium is then diverted to the passageway where the fluid medium contacts the activation material; and inserting the puncture tip of the needle cannula through skin of a patient to allow the fluid medium to flow through the needle cannula;

wherein the fluid medium flows through the needle cannula causing the activation material to expand, contract, or otherwise change in dimension upon direct contact with the fluid medium, thereby releasing the shielding member from the first position, the method further comprising providing capillary tubes within the passageway of the housing and in fluid communication with the needle cannula for diverting the fluid medium from the needle cannula to the activation material.

15. The method as in claim 14, further comprising removing the puncture tip of the needle cannula from the patient, thereby allowing the shielding member to be biased to the second position to cover the puncture tip of the needle cannula.

16. The method as in claim 14, wherein the shielding needle assembly further comprises an interference engagement between the shielding member and the housing and the activation material is associated with the interference engagement, and wherein the fluid medium flow through the needle cannula expands, contracts, or otherwise changes in dimension the activation material, thereby releasing the interference engagement between the shielding member and the housing and allowing the shielding member to be biased toward the second position.

17. The method as in claim 16, further comprising diverting a portion of the fluid medium flowing through the needle cannula to the activation material thereby causing the activation material to expand, contract, or otherwise change in dimension and release the interference engagement between the shielding member and the housing.

18. The method as in claim 16, wherein the expansion, the contraction, or the otherwise change in dimension of the activation material causes an actuator to release the interference engagement between the shielding member and the housing.

19. The method as in claim 14, wherein the fluid medium comprises blood.

\* \* \* \* \*

UNITED STATES PATENT AND TRADEMARK OFFICE
CERTIFICATE OF CORRECTION

PATENT NO. : 9,924,898 B2  
APPLICATION NO. : 12/103322  
DATED : March 27, 2018  
INVENTOR(S) : Charles G. Hwang et al.

Page 1 of 1

It is certified that error appears in the above-identified patent and that said Letters Patent is hereby corrected as shown below:

In the Claims

Column 12, Line 37, Claim 1, delete "position. The" and insert -- position, the --

Signed and Sealed this  
Nineteenth Day of June, 2018

Andrei Iancu  
*Director of the United States Patent and Trademark Office*